United States Patent
Hadjicostis

(10) Patent No.: US 8,702,609 B2
(45) Date of Patent: Apr. 22, 2014

(54) IMAGE-GUIDED INTRAVASCULAR THERAPY CATHETERS

(75) Inventor: Andreas Hadjicostis, Carmel, IN (US)

(73) Assignee: Meridian Cardiovascular Systems, Inc., Carmel, IN (US)

( * ) Notice: Subject to any disclaimer, the term of this patent is extended or adjusted under 35 U.S.C. 154(b) by 1421 days.

(21) Appl. No.: 12/122,456

(22) Filed: May 16, 2008

(65) Prior Publication Data

US 2009/0030312 A1    Jan. 29, 2009

Related U.S. Application Data

(60) Provisional application No. 60/962,169, filed on Jul. 27, 2007.

(51) Int. Cl.
*A61B 8/00* (2006.01)

(52) U.S. Cl.
USPC .......................................................... 600/439

(58) Field of Classification Search
USPC ............... 128/660.03, 662.06, 654, 786, 642, 128/660.04, 660.05, 916; 606/27; 607/122; 600/440, 439, 463, 467, 471
See application file for complete search history.

(56) References Cited

U.S. PATENT DOCUMENTS

| | | |
|---|---|---|
| 3,827,115 A | 8/1974 | Bom |
| 3,938,502 A | 2/1976 | Bom |
| 4,446,395 A | 5/1984 | Hadjicostis |
| 4,532,924 A | 8/1985 | Auth et al. |
| 4,643,186 A | 2/1987 | Rosen et al. |
| 4,682,596 A | 7/1987 | Bales et al. |
| 4,794,931 A | 1/1989 | Yock |
| 4,939,826 A | 7/1990 | Shoup |
| 5,010,886 A | 4/1991 | Passafaro et al. |
| 5,098,431 A | 3/1992 | Rydell |
| 5,176,141 A | 1/1993 | Bom et al. |
| 5,240,003 A | 8/1993 | Lancee et al. |
| 5,291,893 A | 3/1994 | Slayton |
| 5,327,905 A * | 7/1994 | Avitall .......................... 600/585 |
| 5,359,760 A | 11/1994 | Busse et al. |

(Continued)

FOREIGN PATENT DOCUMENTS

| | | |
|---|---|---|
| EP | 1717601 | 2/2008 |
| KR | 10-2006-0112244 | 10/2006 |
| WO | WO9745157 A1 | 12/1997 |
| WO | WO 99/12489 | 3/1999 |

OTHER PUBLICATIONS

Bom, N. et al., "Intra-Arterial Ultrasonic Imaging for Recanalization by Spark Erosion", Ultrasound in Med. & Biol., vol. 14, No. 4, pp. 257-261, 1988.

(Continued)

*Primary Examiner* — Elmer Chao
(74) *Attorney, Agent, or Firm* — Timothy E. Siegel Patent Law, PLLC; Timothy E. Siegel

(57) ABSTRACT

An intravascular ultrasound catheter having an imaging array and ablation electrodes is provided. The imaging array and ablation electrodes are forward facing and the catheter can be used to ablate plaque in partially or totally occluded blood vessels under real time ultrasound visualization. The ablation electrodes are integrated into the distal face of the catheter and allow ultrasound to pass through them, which provides the ability to achieve highly accurate real time visualization of the tissue undergoing treatment.

10 Claims, 11 Drawing Sheets

(56) References Cited

U.S. PATENT DOCUMENTS

| | | | |
|---|---|---|---|
| 5,454,809 A | 10/1995 | Janssen | |
| 5,592,730 A | 1/1997 | Greenstein et al. | |
| 5,622,177 A | 4/1997 | Breimesser et al. | |
| 5,626,576 A | 5/1997 | Janssen | |
| 5,749,914 A | 5/1998 | Janssen | |
| 5,771,895 A | 6/1998 | Slager | |
| 5,788,636 A | 8/1998 | Curley | |
| 5,840,030 A | 11/1998 | Ferek-Petric et al. | |
| 5,840,031 A * | 11/1998 | Crowley | 600/440 |
| 5,857,974 A | 1/1999 | Eberle et al. | |
| 5,893,832 A | 4/1999 | Song | |
| 5,924,993 A | 7/1999 | Hadjicostis et al. | |
| 5,935,108 A | 8/1999 | Katoh et al. | |
| 5,947,905 A | 9/1999 | Hadjicostis et al. | |
| 6,066,096 A | 5/2000 | Smith et al. | |
| 6,356,790 B1 * | 3/2002 | Maguire et al. | 607/102 |
| 6,394,956 B1 | 5/2002 | Chandrasekaran et al. | |
| 6,560,472 B2 | 5/2003 | Hill et al. | |
| 6,582,369 B1 | 6/2003 | Huang et al. | |
| 6,582,423 B1 | 6/2003 | Thapliyal et al. | |
| 6,679,845 B2 | 1/2004 | Ritter et al. | |
| 6,709,396 B2 | 3/2004 | Flesch et al. | |
| 6,783,497 B2 | 8/2004 | Grenon et al. | |
| 6,852,109 B2 | 2/2005 | Winston et al. | |
| 6,858,006 B2 | 2/2005 | MacCarter et al. | |
| 6,892,438 B1 | 5/2005 | Hill et al. | |
| 6,899,682 B2 | 5/2005 | Eberle et al. | |
| 6,925,693 B2 | 8/2005 | Takeuchi et al. | |
| 6,962,567 B2 | 11/2005 | Eberle et al. | |
| 6,972,018 B2 | 12/2005 | Ryan et al. | |
| 6,994,674 B2 | 2/2006 | Sheljaskow et al. | |
| 7,004,940 B2 | 2/2006 | Ryan et al. | |
| 7,022,088 B2 | 4/2006 | Keast et al. | |
| 7,053,530 B2 | 5/2006 | Baumgartner et al. | |
| 7,060,033 B2 | 6/2006 | White et al. | |
| 7,066,895 B2 | 6/2006 | Podany | |
| 7,074,218 B2 | 7/2006 | Washington et al. | |
| 7,112,196 B2 | 9/2006 | Brosch et al. | |
| 7,115,092 B2 | 10/2006 | Park et al. | |
| 7,156,812 B2 | 1/2007 | Seward et al. | |
| 7,156,938 B2 | 1/2007 | Baumgartner et al. | |
| 7,195,179 B2 | 3/2007 | Miller et al. | |
| 7,226,417 B1 | 6/2007 | Eberle et al. | |
| 7,519,410 B2 * | 4/2009 | Taimisto et al. | 600/374 |
| 2004/0147920 A1 * | 7/2004 | Keidar | 606/34 |
| 2004/0254471 A1 | 12/2004 | Hadjicostis et al. | |
| 2004/0254570 A1 | 12/2004 | Hadjicostis et al. | |
| 2005/0033182 A1 | 2/2005 | Cerofolini | |
| 2005/0107783 A1 * | 5/2005 | Tom et al. | 606/47 |
| 2005/0159739 A1 * | 7/2005 | Paul et al. | 606/41 |
| 2005/0251127 A1 | 11/2005 | Brosch et al. | |
| 2006/0030844 A1 | 2/2006 | Knight et al. | |
| 2007/0167804 A1 | 7/2007 | Park et al. | |

OTHER PUBLICATIONS

Karaman, Mustafa, et al., "A Phase Aberration Correction Method for Ultrasound Imaging", IEEE Transactions on Ultrasonics, Ferroelectrics, and Frequency Control, vol. 40, No. 4, Jul. 1993, pp. 275-282.

Slager, Cornelis J. et al., "Vaporization of Atherosclerotic Plaques by Spark Erosion", JACC vol. 5, No. 6, Jun. 1985, pp. 1382-1386, American College of Cardiology.

PCT/US2008/071006 Written Opinion and International Search Report.

* cited by examiner

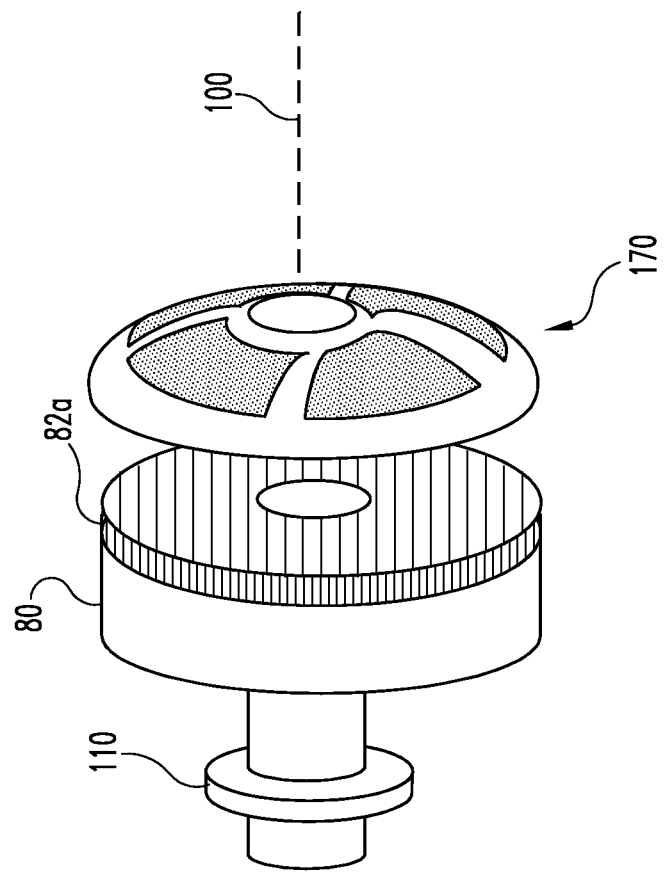
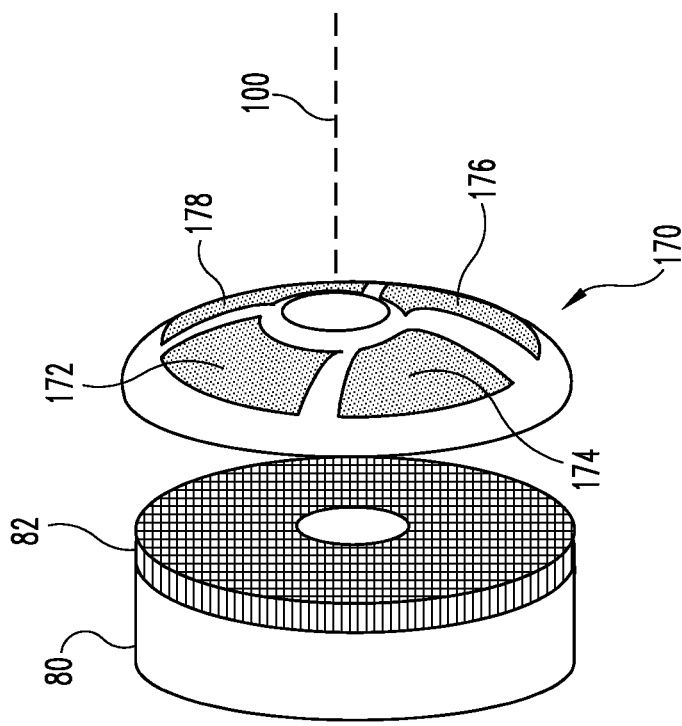
Fig. 7
Fig. 6

IMAGE-GUIDED INTRAVASCULAR THERAPY CATHETERS

RELATED APPLICATION DATA

This application claims the benefit of U.S. Provisional Application Ser. No. 60/962,169 filed Jul. 27, 2007, which is incorporated by reference.

BACKGROUND

This application relates to ultrasonic imaging catheters for medical use. More particularly, but not exclusively, it relates to intravascular catheters having a high frequency ultrasound imaging array that is capable of providing high quality, real-time, forward looking images. Alternatively or in addition, this application relates to catheters that incorporate "see-through" ablation electrodes in front of an ultrasound imaging array so as to facilitate image guided therapy inside a body lumen.

Intravascular ultrasound (IVUS) has been successfully implemented as a visualization tool to assist in the diagnosis and treatment of vascular diseases. (see e.g. *Intracoronary Ultrasound*, by Gary S. Mintz, MD, Taylor & Francis, 1995). However, existing intravascular ultrasound imaging devices designed for use in small lumens (e.g. coronary blood vessels) have either been unable to image in the forward direction or produced images of relatively poor quality. Furthermore, even though the addition of therapeutic ablation functionality into an ultrasound imaging catheter has generally been proposed, commercially available IVUS catheters lack any such therapeutic functionality. Accordingly, there is a need for intravascular devices having improved imaging capabilities and there is also a need for intravascular devices that successful integrate high quality imaging with the provision of ablation therapy. The present application provides systems and techniques for addressing one or both of those needs.

Particular catheters are described herein for use in treating obstructions in partially or totally occluded vessels, for example in peripheral or coronary arteries. These catheters combine miniature high frequency ultrasonic imaging arrays with "see through" RF electrodes such that the operator may enjoy substantially unobstructed direct visualization of the area undergoing treatment. In a preferred form, both the electrodes and the array are forward facing, and the catheter may be used to tunnel through arterial obstructions under real time visualization.

SUMMARY

One embodiment described herein is a unique high frequency ultrasound imaging multi-dimensional array that can be utilized intravascularly to produce high quality real time forwarding looking images of obstructions in blood vessels. As used herein, a multi-dimensional array is an array that has elements arranged in more than a single dimension, such as a 1.5D, 1.75D or 2D array. Multi-dimensional arrays are capable of providing spatial resolution within a volumetric field of view without needing to be relatively translated (e.g. articulated side to side or rotated). Other embodiments described herein may be implemented with a 1D array, which may be rotatable so as to provide a spatial resolution of a volumetric filed of view. Still other embodiments include unique methods, systems, devices and apparatus for generating and detecting ultrasound imaging information to provide real time guidance during an ablation procedure.

One object of the present invention is to provide unique multi-dimensional ultrasound arrays for high frequency intravascular ultrasound applications.

Another object is to provide a unique catheter system that incorporates both high frequency ultrasound visualization and selective ablation capabilities in a manner that facilitates the visualization and treatment of occluded vessels.

Another object is to provide a unique catheter system that combines forward looking ultrasound visualization with forward facing ablation electrodes that are substantially transparent to the ultrasound.

Further forms, objects, features, aspects, benefits, advantages, and embodiments, of the present invention shall become apparent from the detailed description and drawings provided herewith.

BRIEF DESCRIPTION OF THE FIGURES

FIG. 6 is a view showing the incorporation of a smoothly curved tip with the 2-D array of FIG. 3.

FIG. 7 is a view showing the incorporation of a smoothly curved tip with the rotatable 1-D array of FIG. 4.

DETAILED DESCRIPTION OF THE DISCLOSED EMBODIMENTS

Figure 1:
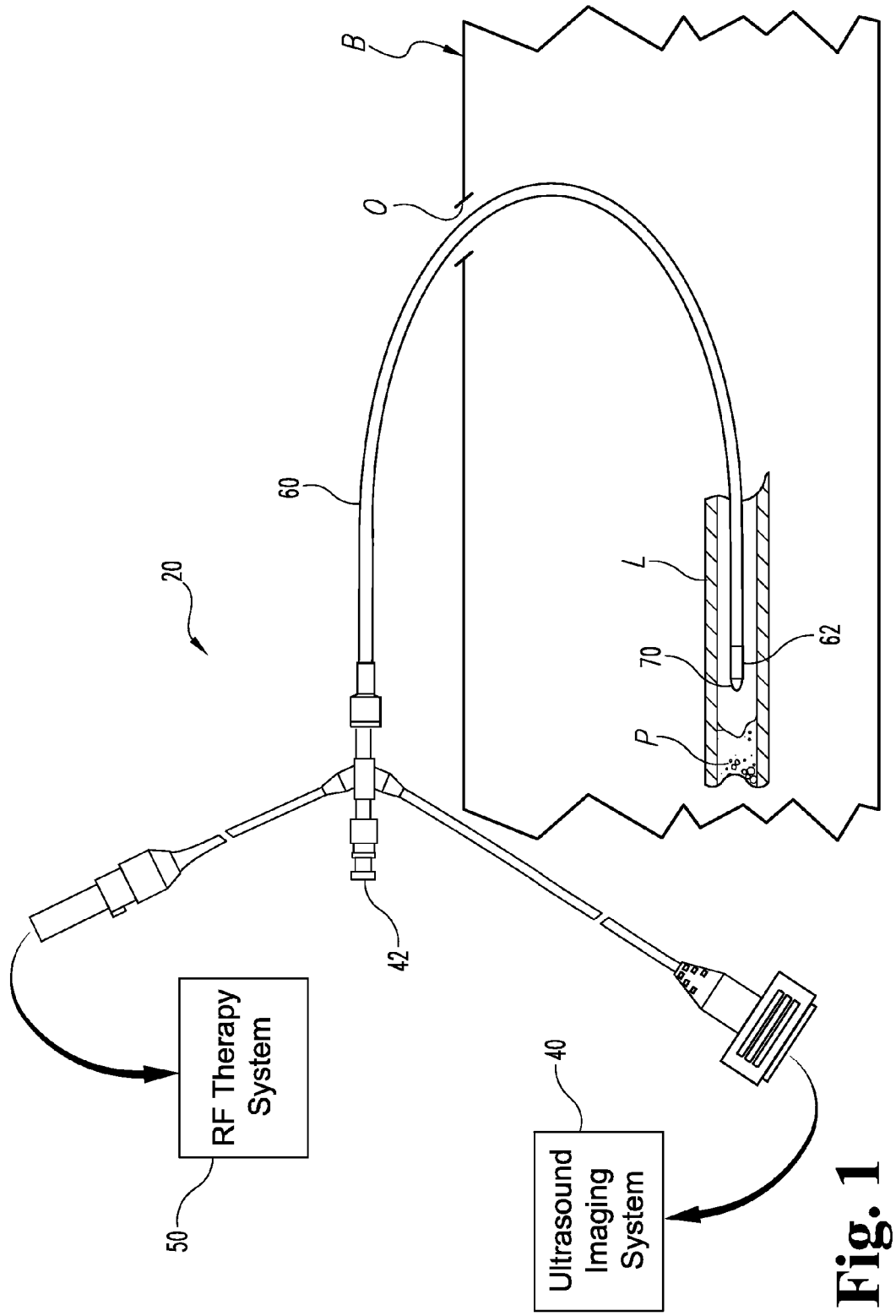
FIG. 1 is a schematic view of a catheter system utilizing ultrasound and RF therapy.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

One embodiment of the present invention includes an ultrasonic device structured for percutaneous insertion in the human body. The device includes an array of piezoelectric elements located at a distal end portion and cabling, connected to the array, that extends to a proximal end portion of the device and connects to an ultrasound imaging system. The elements in the array are designed to send and/or receive high frequency (e.g. about 15 MHz and above) ultrasound for volumetric image generation. In a preferred form, the elements are in the form of a densely packed 2-D array, for example with individual elements having length and width dimensions each less than 100 µm (i.e. element density of at least 100 elements per square millimeter), suitable for producing high quality 3-D images of an interrogated volume. Preferably the element dimensions are in the range of about 50 µm×50 µm for an element density of about 400 elements per square millimeter. This miniature densely packed array provides high resolution imaging information yet is small enough to be used in a variety of diagnostic and therapeutic applications including, but not limited to, intravascular ultrasound visualization.

In one contemplated application, the transducer elements are positioned in a catheter so as to provide a forward facing view of tissue that is adjacent the distal tip. A number of RF ablation electrodes are incorporated on the distal tip, and cabling connected to the electrodes extends through the catheter to a proximal end portion and connects to an RF therapy system. The RF electrodes are configured to be used to ablate tissue when the operator determines, based on the ultrasound imaging information provided in real time by the array, that tissue ablation is necessary or appropriate.

In a preferred aspect, the transducer array and the electrodes are configured such that the ultrasound imaging occurs, at least partially, through the RF electrodes. The RF electrodes are positioned directly in the path of the ultrasound interrogation but are constructed such that they do not unduly attenuate the ultrasound. Rather, the electrodes comprise electrically conducting layers that are sufficiently thin that they pass a substantial fraction of the ultrasound at the relevant frequency, which is preferably in the range of 20-40 MHz, such as about 25 MHz. Modeling has confirmed that a 1-2 µm thick layer of certain metals, such as gold, titanium, aluminum, magnesium or beryllium for example, would be sufficiently transparent to ultrasound at 25 MHz. It is believed that in practice electrodes comprising up to about 8 µm thickness of these metallic conductors would also be adequately transparent to high frequency ultrasound such that imaging can occur through the electrodes.

Certain embodiments described herein may be specifically configured for use in passing vascular occlusions. One such device includes an intravascular catheter having a proximal end, a distal end, and a distal tip. The ablation electrodes are positioned on the distal tip and an ultrasound array is located at the distal end of the catheter proximal to the electrodes. The catheter is configured to be delivered to a site of an occlusion and the array is configured to provide real-time imaging of the occlusion by transmitting and receiving ultrasound through the electrodes. The electrodes are configured to be selectively operated to deliver energy to ablate the occlusion. In use real-time images of the occlusion and the surrounding vascular walls are displayed on a monitor and the operator activates the RF electrodes to ablate plaque while advancing the catheter through the occlusion.

General System Design

With reference to FIG. 1, further aspects are described in connection with system 20. System 20 is arranged to provide images internal to body B for medical diagnosis and/or medical treatment. System 20 includes a control station comprising an ultrasound imaging system 40 and an RF therapy system 50, each of which are operatively coupled to probe device 60, as well as appropriate operator input devices (e.g. keyboard and mouse or other pointing device of a standard variety) and operator display device (e.g. CRT, LCD, plasma screen, or OLED monitor).

Figure 10:
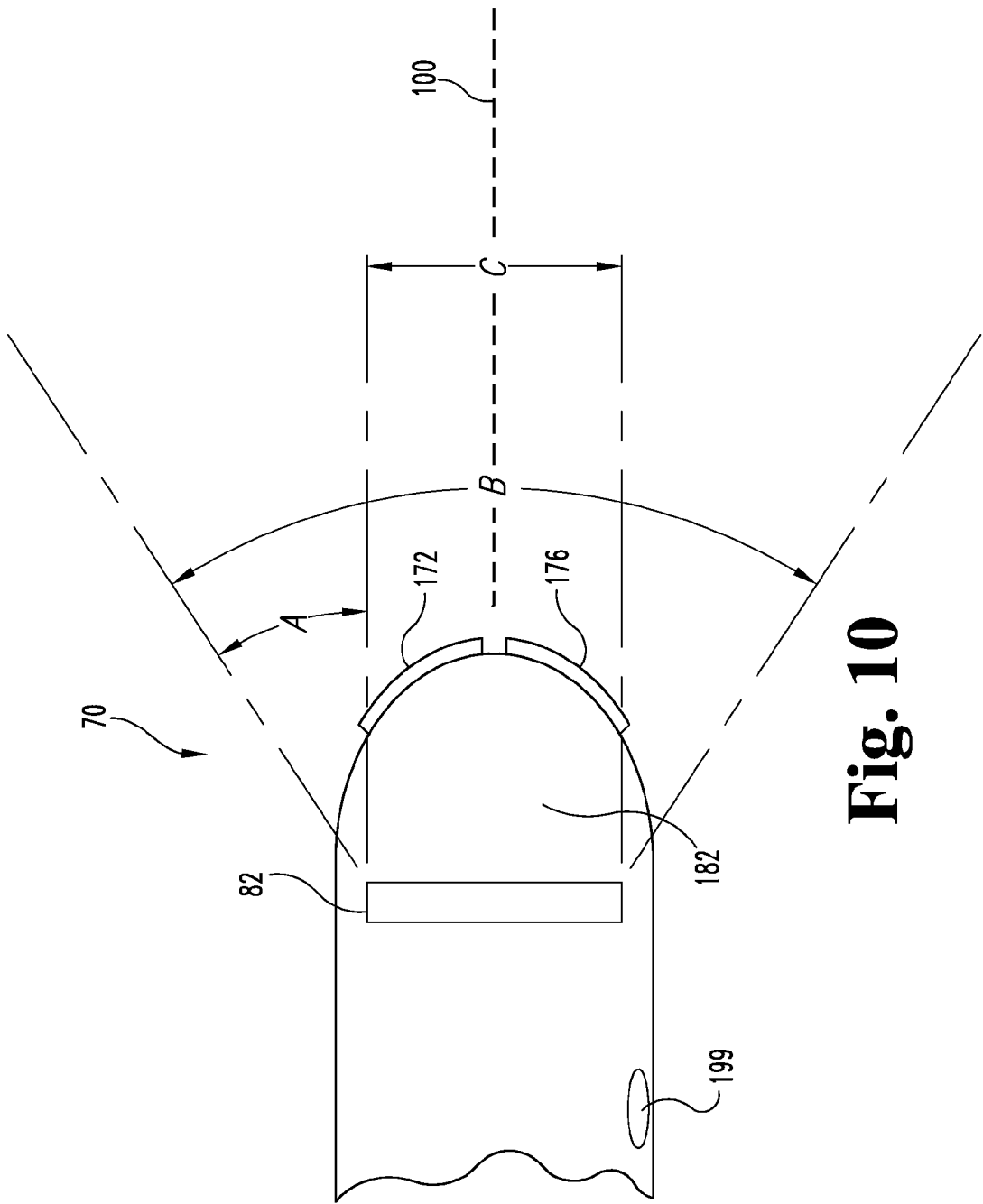
FIG. 10 is a schematic side view of a catheter incorporating the smoothly curved tips of FIG. 6 or 7.

Device 60 is configured for placement through opening O and into body B of a human patient or subject, as schematically represented in FIG. 1. Device 60 is preferably configured for insertion into a blood vessel or similar lumen L of the patient by any conventional vascular insertion technique. As illustrated in FIG. 1, device 60 includes a guide wire lumen that extends from a proximal port 42 through the distal tip 70 of the device 60, which is used to insert device 60 over a pre-inserted guidewire (not shown) via a conventional over the wire insertion technique. The guidewire exit port 199 may be spaced proximally from the distal tip, as illustrated in FIG. 10. Device 60 may be configured with a shortened guidewire lumen so as to employ a monorail type insertion technique, or device 60 may be configured without any guidewire lumen and instead configured for insertion through the lumen of a pre-inserted guide catheter.

Referring to the schematic illustration of FIG. 10, distal tip 70 generally includes at least one imaging array 82 capable of imaging vascular tissue and one or more therapy electrodes 172, 176 capable of applying therapy to vascular tissue. The array 82 is contained within tip 70 and is spaced proximally from electrodes 172, 176, which are deposited on the outer surface of tip 70. Both the array 82 and electrodes 172, 176 define operative surfaces that are non-parallel to the longitudinal axis 100 of tip 70, which is to say they are each "forward facing." This allows the device to be used to image and treat vascular occlusions or plaque P in front of the tip. Optionally, one or more side facing electrodes and/or a side facing array may be included to allow the device 60 to be used to image and/or treat vascular structures to the side.

The array 82 is preferably configured to interrogate a volumetric image field, which refers to the interrogated volume within which imaging information can be derived. As illustrated, array 82 is a 2-D array oriented generally orthogonal to the longitudinal axis 100 of the distal tip 70. In this arrangement, array 82 defines an image field that is generally conically shaped and centered about the longitudinal axis 100, as indicated by solid angle B. The image field of array 82 includes the central area (indicated by C) that is orthogonal to the operative face of the array 82 as well as the peripheral area encompassed within the angle of acceptance A. Other configurations and arrangements for the imaging array are contemplated as described more fully herein.

The electrodes 172, 176 are positioned in the image field but, as noted above, are constructed such that the ultrasound transmitted by array 82 can pass through them, which may generally be accomplished by limiting the thickness of the metallic conductor to less than 8, 7, 6, 5, 4, 3, or 2 µm. Because the electrodes 172, 176 are effectively transparent to the ultrasound, the electrodes may cover a substantial fraction of the distal portion of tip 70 so as to provide a wide area of potential treatment without detracting from the ability of the array 82 to image the relevant tissue. For example, it is contemplated that electrodes 172, 176 may collectively cover 50%-90% of the cross sectional area C in front of array 82.

It is to be understood that the general shape of the field of view B depends on the configuration of the array and how the array is incorporated into the catheter. Various modifications may be employed to alter the size, shape, or orientation of the field of view. For example, array 82 is illustrated with an operative (distal) surface that is planar. The operative surface of array 82 may be outwardly curved or convex, which would have the effect of enlarging the boundaries of the cross sectional area C and possibly also increasing the angle of acceptance A. Array 82 may alternatively be of concave shape, which would have the effect of narrowing the field of view.

Alternatively or in addition, the distal portion 182 of catheter tip 70 may be constructed so as to influence the field of view. In one preferred implementation, distal portion is constructed so as to operate as an ultrasound lens. For example, portion 182 may be constructed of a material that transmits ultrasound slower than the surrounding environment (e.g. body tissues) such that the beam is drawn inwardly and focused as the ultrasound passes through the distal tip portion 182. Alternatively portion 182 may be constructed of a material that transmits ultrasound faster than the surround environment so that ultrasound is defocused as it translates through the distal tip. When operating as an ultrasound lens, the radius of curvature of the outer surface of portion 182 would influence the focal length, and the radius of curvature would typically be on the order of the overall diameter of the distal tip. For example, for a 4F catheter (1.273 mm diameter), the radius of curvature of portion 182 may be 1.5 mm.

In still further alternatives, the field of view may by altered by articulating the multi-dimensional array 82 within the distal tip 182. For example, rather than having array 82 stationary inside tip 70, array 82 may be mounted on the end of a micromanipulator such that the orientation of the array 82 relative to the longitudinal axis 100 may be altered. U.S. Pat. No. 7,115,092 describes a micromanipulator that may be adapted for use in articulating a 2-D array.

Figure 4:
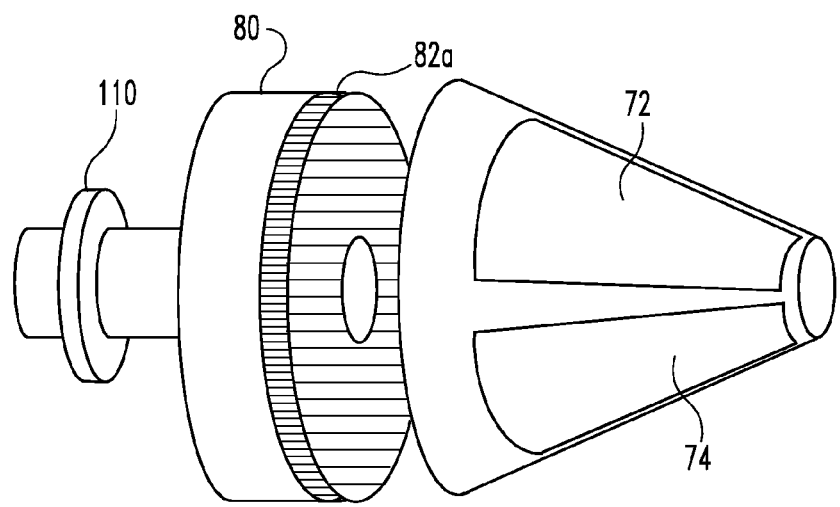
FIG. 4 is a view showing the incorporation of a rotatable ultrasound 1-D array in the distal tip of the FIG. 1 catheter with the acoustic matching layers removed for clarity.

As an alternative to a multi-dimensional array (e.g. a 1.5D, 1.75 or 2D array), a 1-D array may be employed to produce imaging information. FIG. 4 schematically illustrates a 1-D array implementation wherein the array is mounted on a shaft and a motor 110 or similar rotation mechanism is configured to rotate the array so as to acquire a volumetric (3-D) image. In practice, it may take a longer period of time to acquire a 3-D image using a mechanically rotated 1-D array than it would for, for example, a stationary 2-D array.

It is also to be understood that device 60 may be sized as appropriate for the intended application. When adapted for use in coronary arteries, at least the distal portion of device 60 would typically have an outer diameter ranging from 0.75 mm to 3 mm. When adapted for use in treating peripheral artery disease, the outer diameter of the distal tip 70 may be in the range of 1 to 5 mm. The overall length of the catheter may typically be about 150 cm.

To facilitate incorporation of the array 82 with its associated electrical components inside tip 70, a flex circuit interconnection technique may be employed. Suitable flex circuits and useful techniques for mounting piezoelectric arrays on flex circuits are generally known and described in, for example, U.S. Pat. No. 7,226,417 to Eberle and US 2004/0254471 to Hadjicostis et al.

Figure 2:
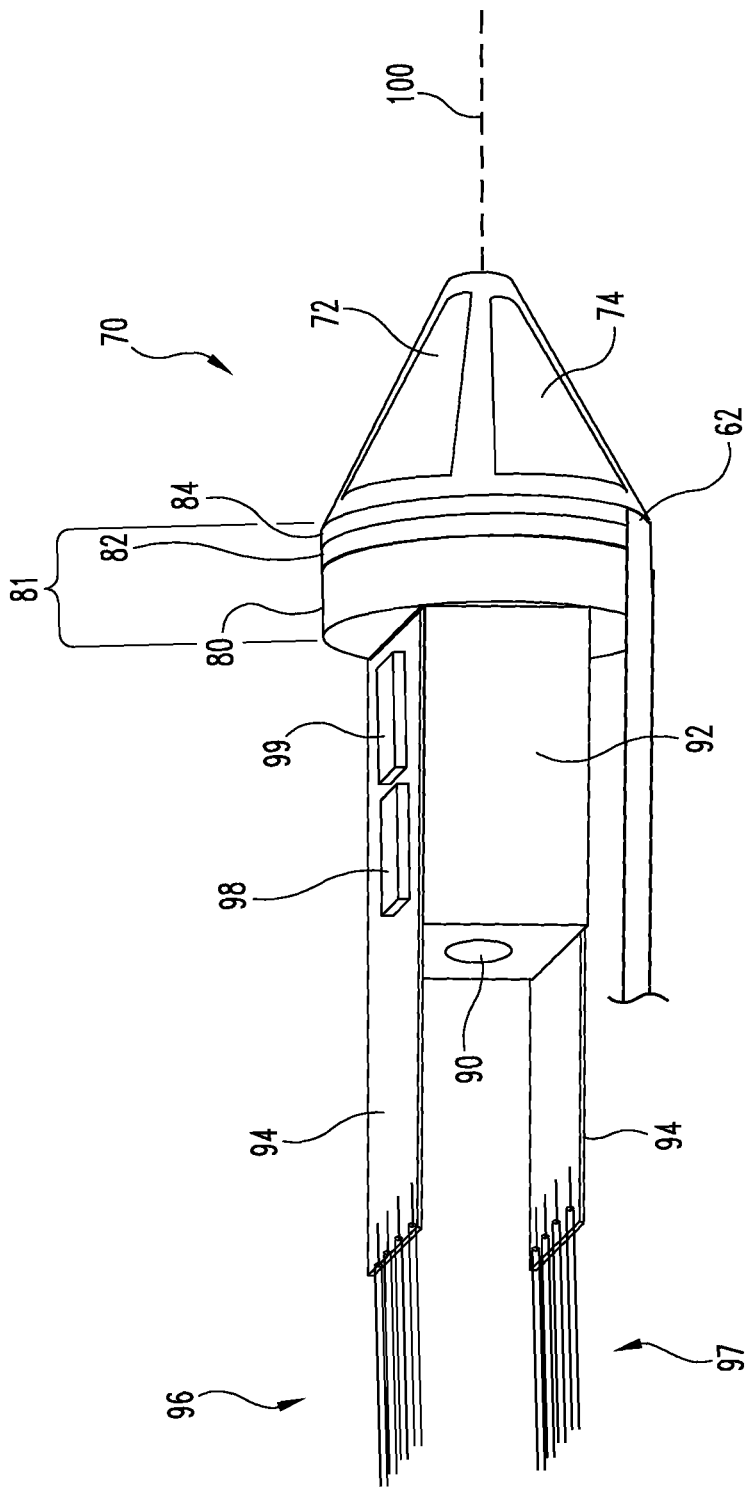
FIG. 2 is a view of the distal tip of the FIG. 1 catheter with the outer sheath shown in partial cutaway for clarity.

Referring now to FIG. 2, an array assembly 81 according to one embodiment includes the array of piezoelectric elements 82, an acoustic backing layer 80, and one or more acoustic matching layers 84. The array assembly 81 is mounted to a flexible circuit substrate 94, which comprises a flexible substrate material (e.g. a polyimide film) and metallic interconnection circuitry (not shown). The interconnection circuitry comprises conductor lines deposited upon the surface of the flex circuit 94 which couples the array 82 to one or more integrated circuit chips 98, 99 each of which incorporates appropriate multiplexers, pre-amplifiers and other electrical integrated circuits such as filters, signal conditioners et al. Ultrasound cabling 96 runs proximally to electrically connect the flex circuit 94 to the ultrasound imaging system 40. The RF electrodes 72, 74, which are shown deposited on a conical distal tip, are also electrically connected to the flex circuit 94 via wires (not shown) that run through or around the array assembly 81, and RF cabling 97 electrically connects the flex circuit 94 to the RF therapy system 50. An outer sheath 62 (shown in partial cutaway for clarity) surrounds the array assembly 81 and the remainder of the components that are proximal to the electrodes 72, 74.

The flex circuit 94 is attached to a marker 92. Marker 92 provides structural rigidity to facilitate assembly, and marker 92 may be constructed of radio-opaque material and used to facilitate fluoroscopic visualization of the catheter tip.

Imaging System

Imaging system 40 is configured for generating and processing signals and data associated with the ultrasound transducers array 82 contained in the distal tip 70 of device 60. The transducer array 82 is preferably a multi-dimensional imaging array capable of producing high quality 3-D visualization information, and array 82 is preferably constructed by dicing a piezoelectric workpiece into the appropriate number of elements as described herein. However, system 20 may be usefully implemented with a number of different imaging arrays known in the art, for example those described in U.S. Pat. Nos. 5,857,974 and 6,962,567 to Eberle et al., U.S. Pat. No. 6,994,674 to Shelgaskow et al., and/or U.S. Pat. No. 7,156,812 to Seward et al.

Imaging system 40 connects to a co-axial cable bundle 96 that includes analog signal lines and digital control wires for bidirectional communication with array 82 via flex circuit 94. The ultrasound coaxial bundle 96 may comprise analog miniature co-axial cables (each of which typically has diameter 46-54 AWG). The gauge of the digital control wires may be about 42-50 AWG. The number of analog lines may vary from 16 to 128 with the preferred embodiment being 32 to 64. The digital control lines may typically vary from be 5-20. The ultrasound cable bundle 96 terminates proximally in a multi-pin connector for ease of interface with the ultrasound imaging system 40. The multiplexers in the chips 98, 99 allow the system 40 to be able to separately address each individual element (if desired) even though the number of analog signal lines in bundle 96 may be substantially less than the number of elements in the array.

Subsystem 40 may include analog interface circuitry, Digital Signal Processors (DSP), data processors, and memory components. For example, analog interface circuitry may be responsive to control signals from DSP to provide corresponding analog stimulus signals to imaging device 60. The analog circuitry and/or DSP may be provided with one or more digital-to-analog converters (DAC) and one or more analog-to-digital converters (ADC) to facilitate operation of system 20 in the manner to be described in greater detail hereinafter. The data processor may be coupled to the DSPs to bi-directionally communicate therewith, to selectively provide output to the display device, and to selectively respond to input from the operator input devices.

The DSPs and processors perform in accordance with operating logic that can be defined by software programming instructions, firmware, dedicated hardware, a combination of these, or in a different manner as would occur to those skilled in the art. For a programmable form of DSPs or processors, at least a portion of this operating logic can be defined by instructions stored in a memory, which can be of a solid-state variety, electromagnetic variety, optical variety, or a combination of these forms. Programming of the DSPs and/or processors can be of a standard, static type; an adaptive type provided by neural networking, expert-assisted learning, fuzzy logic, or the like; or a combination of these.

The circuitry, DSPs, and processors can be comprised of one or more components of any type suitable to operate as described herein. Further, it should be appreciated that all or any portion of the circuitry, DSPs, and processors can be integrated together in a common device, and/or provided as multiple processing units, and/or that one or more signal filters, limiters, oscillators, format converters (such as DACs or ADCs), power supplies, or other signal operators or conditioners may be provided as appropriate to operate system 20 in the manner to be described in greater detail hereinafter. Distributed, pipelined, and/or parallel processing can be utilized as appropriate.

The imaging system activates the transducer array to acquire 3-D imaging information by any number of techniques known in the art based on the configuration of the array. For example, the array 82 may be operated as a sparse array or as a fully sampled array. The array may be phased in one or both dimensions. In one form, the array 82 is operated via a synthetic aperture approach. During synthetic aperture imaging, predefined subsets of the elements in the array are activated in sequence and the resulting responses are collected to form a complete image. This approach may be employed for any type of array (e.g. 1-D or multi-dimensional arrays) wherein the number of elements in the array is much greater than the corresponding number of analog signal lines. For example, if there are 32 analogue lines that are used to drive a 324-element array, then the system 40 is configured to transmit and receive with up to 32 elements at a time. The information from one group elements (e.g. the first 32) is collected and stored, and the processes repeats with another group of elements (e.g. the second 32) until all the elements in the array have been addressed. The total information received from all the elements is then processed to produce a single image frame.

In addition to transmitting and receiving with the subgroups of 32 elements, system 40 may also be implemented to transmit with a first sub group of elements and to receive sequentially with every other sub-group of elements. For a 324 element array, there would be ten (10) 32-element subgroups present with 4 elements not being used. The signals received from all the receiving sub-groups in the array are called "cross products." Collecting the cross products helps to increase overall image quality.

Therapy System

With reference to FIG. 2, which schematically illustrates the distal tip 70 with its proximally extending outer sheath 62 shown partially cutaway, RF Therapy subsystem 50 is designed to generate a current and send the resulting current to one or more therapy electrodes 72, 74 on the distal tip 70 of device 60. The electrodes 72, 74 are a thin metallic layer deposited on the exterior of the front end of the distal tip 70, which may have a conical (FIGS. 3-5) or smoothly curved (FIGS. 6-10) shape. The RF electrodes are electrically connected to conductive traces on the flex circuit 99 and through the flex traces to the catheter cables 97.

A cable bundle 97 connects the RF electrodes 72, 74 to the external electronic driver system, and the RF cable bundle 97 terminates proximally in a multi-pin connector to facilitate connection to the RF Therapy system 50. The number of connections may be in the range of 2 to 10.

The RF system 50 includes voltage controller(s), voltage generator(s), and a current detector(s) as well as appropriate switches and controllers for directing the current to individual ones of the therapy electrodes 72, 74. The voltage controllers set the frequency and amplitude of the voltage produced by the generators as well as its sequencing in time, which may be selected based on preset configurations, information received from the user via an input interface, or measurements performed in the system 50. The current detectors determine the amount of current sent to each therapy electrode. A temperature monitoring system may also be included to receive temperature information from a temperature sensor (not shown) near the therapy electrodes.

The current flowing from the therapy system 50 to a therapy electrode 72, 74 passes to tissue when the electrode is placed adjacent to tissue. This current spreads as it penetrates into the tissue and generates heat according to the local current density, ablating (i.e. removing) the tissue. Without intending to be bound by any theory of operation, it is believed that under appropriate conditions, the ablation process can be carried out such that plaque removal occurs essentially one cell layer at a time, reducing the chances of complications.

The timing and amount of current applied to each electrode is chosen to achieve the desired therapeutic result, which in a contemplated application would involve the controlled erosion of arterial plaque P at a suitably controlled rate of erosion (e.g. one cell layer at a time). For example, it may be preferable to apply energy in the form of short bursts (i.e. 1.0 to 2.5 J delivered over 10 ms) to achieve the spark erosion of plaque as described in Slager, J Am Coll Cardiol 1985; 5:1382-6. Energy may also be generated in the form of a 1 MHz sine wave with a 5%-25% duty cycle with a peak-to-peak voltage of 500-1000 V. The preferred operating frequency of the RF electrodes is in the range of 0.25 to 5 MHz.

RF Electrodes/Tip Construction

The therapy electrodes 72, 74 are forward facing, which allows the device 60 to operate in a tunneling fashion, e.g. so as to be useful in creating a passage through partially or totally occluded arteries. Electrodes 72, 74 are also preferably arranged on the distal tip 70 in spaced relation about the longitudinal axis 100 of the device 60 and configured such that and each electrode can be operated individually. This allows therapy to be applied symmetrically or asymmetrically relative to the longitudinal axis 100 of the distal tip 70 device 60. Symmetric ablation would have the tendency to achieve straight ahead tunneling (i.e. in tunneling in the direction of longitudinal axis of device 60), whereas asymmetric ablation would lead to tunneling in the direction of the electrodes that are activated.

In a preferred implementation, the operator controls the therapy system 50 based on visualization information provided by the imaging system 40. For example, if the operator observes from the ultrasound images that the catheter is nearing a structure that should be avoided (i.e. an arterial wall), the operator can "turn off" or "turn down" the therapy electrodes on one side and/or increase the energy applied to the electrodes on the other side.

The RF therapy electrodes are constructed from a thin layer of gold, titanium, aluminum, magnesium, beryllium or any other metal or metallic material having high electrical conductivity, high sound propagation velocity and/or low density. In one form, the RF electrodes are metallic strips that are sufficiently thin that the ultrasound passes without substantial attenuation or interference, for example having a thickness less than about 8 micrometers, such as in the range of 0.2 to 8 μm, 0.4 to 6 μm, 0.5 to 4 μm, 0.7 to 2 μm, or 0.9 to 1.5 μm. The metallic strips may applied by a vapor deposition technique or any other convention process for forming a thin layer of metallic material.

If the supporting tip surface is constructed of a suitable synthetic material capable of withstanding the high temperatures generated by the electrodes, the electrode material may be deposited or applied directly onto the tip. Suitable synthetic materials include high temperature plastics (e.g. Torlon, available from Solvay Advanced Polymers LLC, Alpharetta, Ga.) or silicone rubber materials (e.g. RTV325, Eager Plastics, Inc. Chicago, Ill. or RTV 560 GE Plastics). Skilled persons will readily recognize that sound travels more slowly through these materials, relative to the speed of sound through water or body tissue.

Alternatively or in addition, a thermal insulating layer 180 (FIGS. 8-9 and 15-16) may be provided to protect the tip 170 from damage from the heat generated by the electrodes. Layer 180 may comprise a thin layer of ceramic (such as $Al_2O_3$) and may be formed as a relatively uniform coating or shell covering the distal face of tip 170. The thickness of this ceramic layer 180 is sufficient to protect the substrate 182 from thermal damage due to heat generated by the electrodes 172, 176, and might be in the range of 0.5-5 micrometers.

Figure 9:
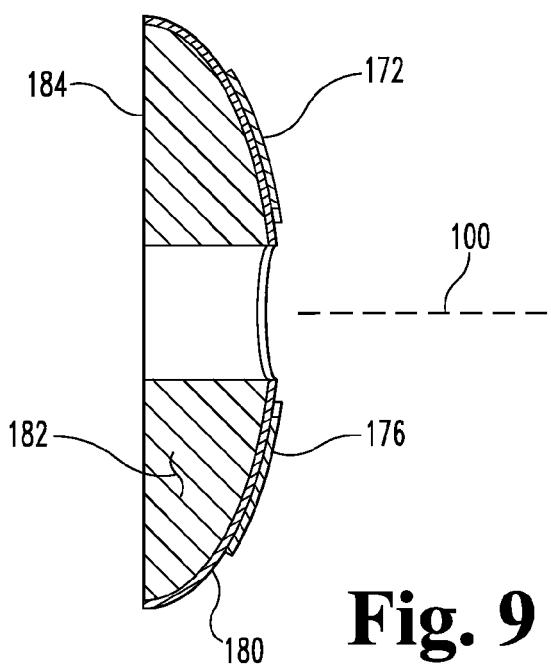
FIG. 9 is a cross sectional view of the smoothly curved tip of FIG. 8
Figure 16:
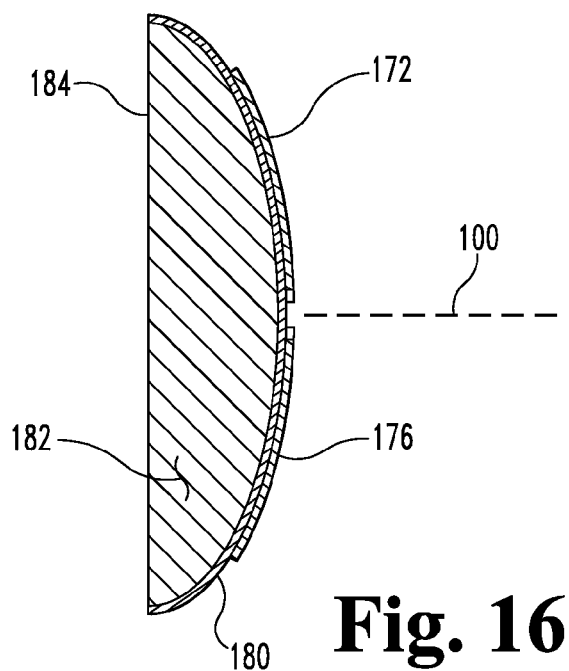
FIG. 16 is a cross sectional view of the smoothly curved tip of FIG. 15

It is to be understood that, as depicted in both FIGS. 9 and 16, the proximal face of tip 170 is designed to be positioned against and acoustically coupled to the distal face of the acoustic stack 81, and consequently the tip 170 as shown in FIG. 9 includes a central lumen that matches guidewire lumen 90. The provision of a central guidewire extending through the distal tip 170 may be beneficial for purposes of control and guidance, but the interruption to the array may degrade image quality. The tip 170 of FIG. 16 is designed for embodiments wherein no guidewire lumen interrupts the array 82, for example, because the guidewire exit 99 is spaced proximal to the array 82 as shown in FIG. 10.

Array Construction

Figure 11:
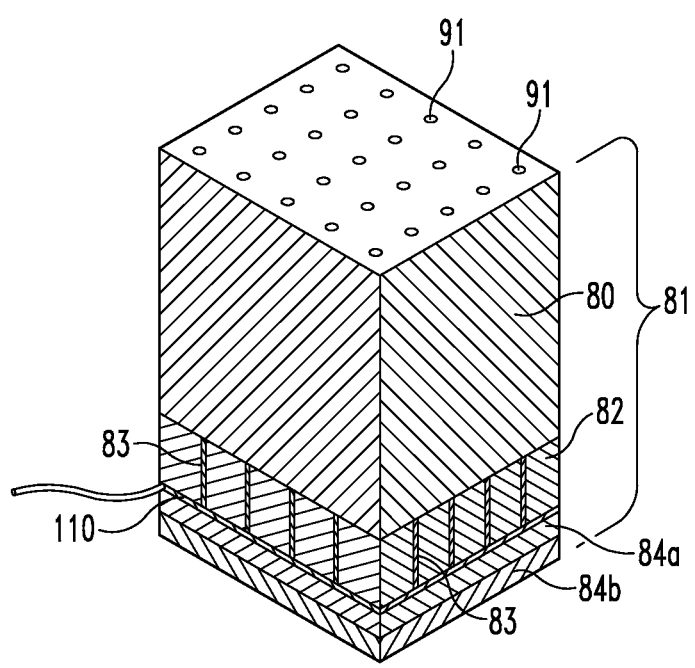
FIG. 11 is a perspective view of a 2-D ultrasound transducer array assembly.

The therapy catheters described herein can be usefully implemented with a number of different imaging arrays constructed according to a number of conventional techniques. It is preferred, however, that the array be very small and operate at high frequency such that extremely high quality 3-D imaging information is provided. Miniature high frequency imaging arrays for use in the present therapy catheters or in any other application where ultrasonic imaging via a miniature high frequency array would be beneficial are described in connection with FIG. 11.

A 2-D acoustic stack 81 includes a diced array of piezoelectric elements 82. The elements are formed by dicing a commercially available piezoelectric work piece, for example, CTS 3257HD (CTS Electronic Components, Inc. Albuquerque, N.M.). A dicing saw is used to make a series of parallel cuts in a first direction (e.g. the X direction) and then in a second direction (e.g. the Y direction) and the resulting kerfs 83 are filled with a suitable epoxy after dicing in each of the directions. A metallizing layer 110 is deposited over the distal face of the piezoelectric elements 82 to serve as a common ground electrode. The proximal face of each of the elements 82 is in electrical contact with individual signal lines 91, which extend through an acoustic backing layer 80. The proximal face of each of the elements 82 may include its own metallizing layer (not shown) to facilitate electrical connection with the individual signal lines 91, and one or more acoustic matching layers 84a, 84b are applied to the distal face of the elements 82. The flex circuit 94 has contact pads (not shown) spatially arranged to correspond to the arrangement of the individual signal lines 91 that are exposed at the proximal face of backing layer 80. Alternatively, elements 82 may be applied directly to the flex circuit 94 and the acoustic backing layer 80 may be applied to the back side of the flex circuit, in which case there is no need for signals lines 80 in the backing layer 80.

Preferably, the array 82 is diced into two directions such that the resulting elements are generally square and the pitch (i.e. the spacing between centers of adjacent elements) is less than 100 μm, preferably less than 75 μm, less than 60 μm, or about 50 μm. The array 82 may be constructed such that it includes at least about 100, 200, 300, 400, 500, 600, or 700 elements. The array 82 may be constructed such that element density is greater than about 100, 200, or 300 elements per $mm^2$.

A useful procedure for producing a diced one dimensional array is described in US 2004/0254471 to Hadjicostis et al, which is incorporated herein for that purpose. Similar techniques can be employed to construct a miniature multi-dimensional array. The main difference would be the introduction of an additional dicing step and the provision of suitable contact pads in the flex.

Additional details of specific embodiments are now described. As noted above, the RF electrodes 72, 74 are electrically connected to conductive traces on the flex circuits 94 and through the flex traces to the catheter cables 97. The RF traces on the flex may have width equal to 15-25 μm and thickness equal to 1-5 μm. The ultrasound and digital lines on the flex circuit 94 may have a width equal to 5-15 μm and thickness equal to 1-3 μm The distal end of the catheter includes the catheter tip and may have an outer diameter in the range of 0.75 to 3 mm for coronary artery treatment. The diameter of the tip may be different than the above range of values for other intravascular uses. For example, for the peripheral arterial system the tip diameter can be in the range of 1-5 mm. The catheter tip incorporates the RF electrodes 72, the ultrasound piezoelectric imaging array 82, a radio-opaque marker 92, flex-circuit interconnects (not shown, on 94), IC multiplex/pre-amp chips 98, 99 and connections to the RF and ultrasound cables.

Figure 3:
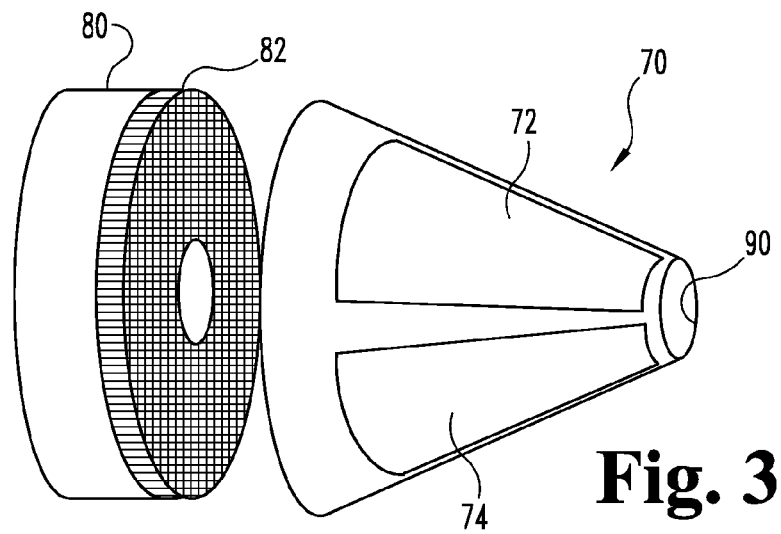
FIG. 3 is a view showing the incorporation of a planar ultrasound 2-D array in the distal tip of the FIG. 1 catheter with the acoustic matching layers removed for clarity.
Figure 5:
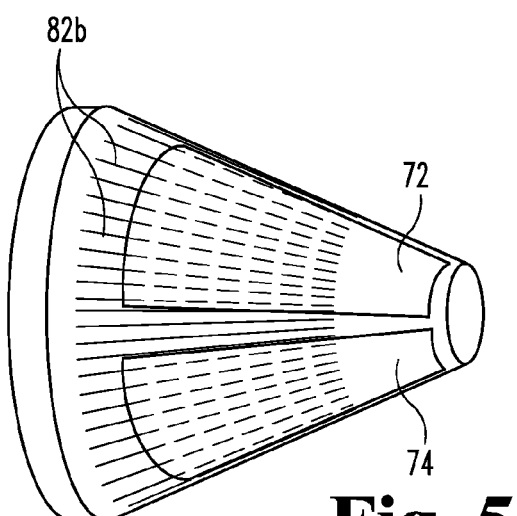
FIG. 5 is a view showing the incorporation of a conical ultrasound array in the distal tip of the FIG. 1 catheter.
Figure 8:
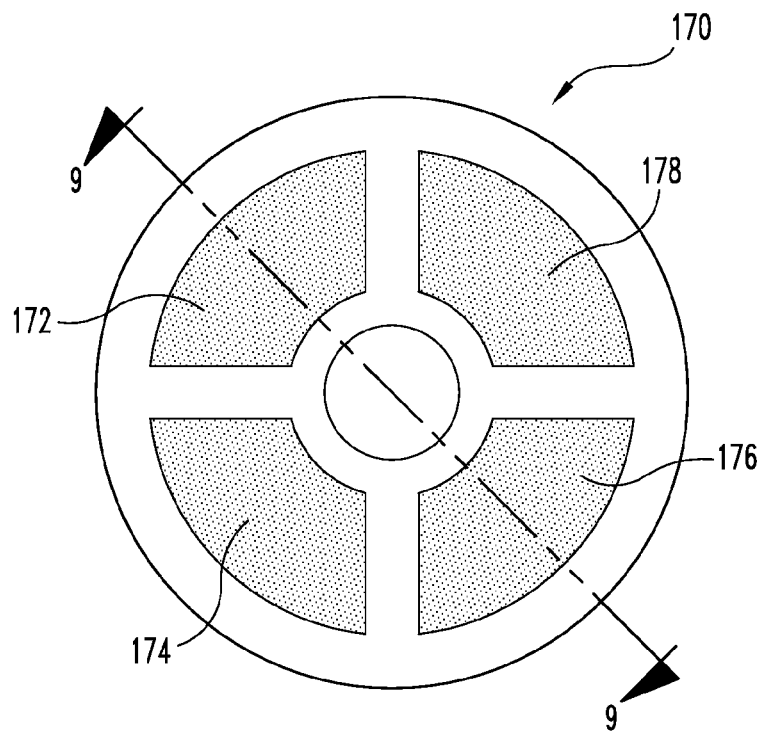
FIG. 8 is an end view of the smoothly curved tip of FIG. 6 or 7 looking proximally along the longitudinal axis 100.

In several of the embodiments (FIGS. 2-5) the distal end of the tip 70 has a generally conical shape with the RF electrodes 72, 74 consisting of a metallic material such as gold, or other metal having high electrical conductivity deposited on top of a solid cone. The cone incorporates an opening 90 to accommodate a guide wire. The preferred material for the conical tip is a high temperature plastic such as Torlon™; however other appropriate materials may also be used. In one embodiment the tip lumen has diameter equal to 0.017"-0.018" in other embodiments the lumen can have diameter of 0.013"-0.014". The RF electrodes are electrically connected to conductive traces on the flex circuits and through the flex traces to the catheter cables. The RF traces on the flex have width equal to 0.015-0.025 mm and thickness equal to 0.001-0.005 mm. The ultrasound and digital lines on the flex have width equal to 0.005-0.015 mm and thickness equal to 0.001-0.003 mm The ultrasound array stack 81 is located distal to the electrodes 72, 74, and may be spaced from the electrodes as shown in FIGS. 3 and 4. Alternatively, the array elements 82b may be arranged on or close to the outer surface of the cone so as to underlay the electrodes 72, 74, as shown in FIG. 5. The array stack 81 may comprise three or four layers: an acoustic backing material 80, a diced piezoelectric ceramic 82, and one or two quarter-wave matching layers 84 (84a, 84b in FIG. 11). The array 82 may be either one-dimensional or two-dimensional. The piezoelectric elements may have −6 dB bandwidth in the range 40%-100% and insertion loss less than −20 dB.

The array of piezoelectric elements are electrically connected to conductive traces on the flex circuits 94 and through the flex traces (not shown) to the catheter cables 96, 97. The flex circuits are mounted onto a radio-opaque marker for mechanical stability. The radio opaque market enables the user to locate the catheter tip employing x-ray detection. Custom integrated circuit (IC) chips 98, 99 are mounted by soldering to the flex circuits 94 using flip chip bonding techniques. These IC chips 98, 99 include circuits that function as multiplexers for the ultrasound signals as well as pre-amplifiers for the return ultrasound signals. The use of the IC chips as multiplexers reduces the number of cables needed to connect the array to the imaging system and the pre-amplifiers enable the effective transmission of ultrasound return signals through the co-axial cables.

FIGS. 3, 4, 5, and 7 illustrate three basic configurations of the acoustic stack. FIG. 3 depicts a planar two-dimensional (2D) array. Such an array may have 100 to 1024 elements and may be multiplexed to the coaxial bundle. A potential benefit of using a 2-D array is that (a) it need not have any moving parts and (b) it has complete flexibility in acquiring 3D images in front of the catheter using electronic focusing and beam control. A potential disadvantage of using a 2D array is the introduction of electronic interconnect complexity by having a large number of elements.

FIG. 4 depicts a one-dimensional array (1D). Such an array may have 16-128 elements and may be configured for rotational motion through the employment of a wire shaft connected to an outside motor (not shown), or via a miniature motor 110 provided inside the catheter adjacent the array. A potential benefit of using a 1-D array is relative ease of construction and electrical interconnect at the expense of introducing mechanical movement, additional mechanical components and longer times to acquire a 3D image. In a given orientation, a 1D array can acquire two-dimensional images of the area in front of the catheter tip. Three-dimensional images can be constructed through an incremental 180 degree rotation of the 1D array, storage of acquired 2D images and then reconstruction of 3D images through integration of the 2D images.

FIG. 5 illustrates yet another arrangement in which the transducer elements 82b are arranged in a conical pattern following the curvature of the conical tip. A conical transducer array can provide images that describe a conical surface perpendicular the cone of the tip. A potential advantage of this configuration is relative simplicity of construction at the expense of the image quality, which may be somewhat deteriorated. The number of array elements 82b in this case may range from 16-128. The RF electrodes 72, 74 in this case lie directly above the ultrasound imaging array 82b.

FIGS. 6-7 illustrate yet another embodiment of the catheter tip. The difference in this approach is that the tip of the catheter is curved. The preferred shape of the curvature is spherical however other types of curved surfaces may be employed such as ellipsoidal, paraboloidal or other. The diameter of the spherical case can be in the range of 1 mm to 10 mm. In a further refinement of the preferred embodiment, the semispherical tip can be coated with a thin ceramic material 180 (such as $Al_2O_3$), which is shown in FIG. 9. The thickness of this ceramic coating may be 0.5-5 micrometers and its purpose is to provide protection to the tip from heat damage. The material 182 of the semispherical tip may be high temperature silicone such as RTV325 produced by Eager Plastics, Inc of Chicago, Ill. Other RTV types can be used, such as RTV 560 from GE in conjunction with the ceramic coating on the lens. The advantage of using a smoothly curved (e.g. semispherical) tip versus a conical tip is that the RTV material 182 can function as an ultrasound lens and therefore produce images of higher resolution and improved quality. The RF electrodes are again made of metal as previously described in the present application.

Yet another embodiment is one which applies in the case of the 2D array. In this case the 2D array itself can be spherically shaped, with the RF electrodes deposited outside the matching layer of the array (not shown). In this case no additional tip is required and the images will have improved sensitivity and quality. However the use of a curved 2D array provides further electronic interconnect complexity.

The preferred operating frequency of the ultrasound array elements is in the range of 15-40 MHz, for example between 20 and 35 MHz, between 20 and 30 MHz, or about 25 MHz. The phased array may have half-wavelength element spacing for optimum ultrasound beam forming. Each element may incorporate quarter wave matching layers for better transfer of power.

EXAMPLES

Reference will now be made to specific examples illustrating certain particular features of inventive embodiments. It is to be understood, however, that these examples are provided for illustration and that no limitation to the scope of the invention is intended thereby.

Figure 12A:
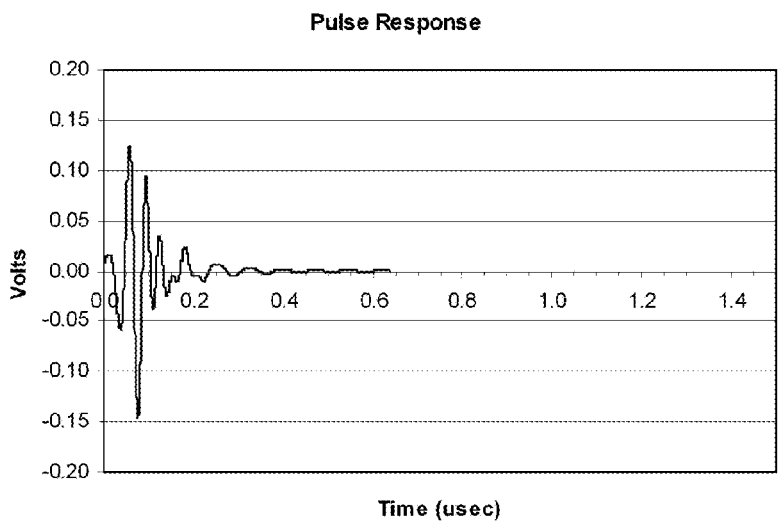
FIGS. 12A-12C are exemplary plots of the pulse response, impedance, and loss for a modeled intravascular transducer array wherein imaging is performed through a catheter tip without any RF electrodes present.
Figure 12B:
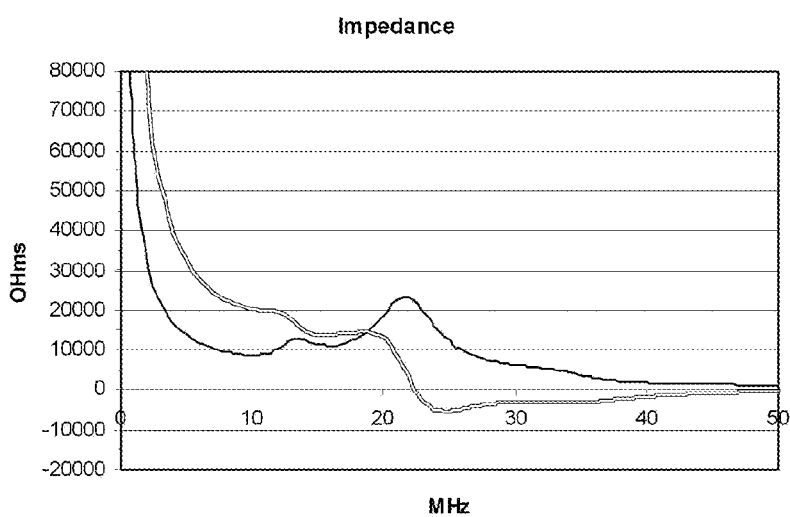
Figure 12C:
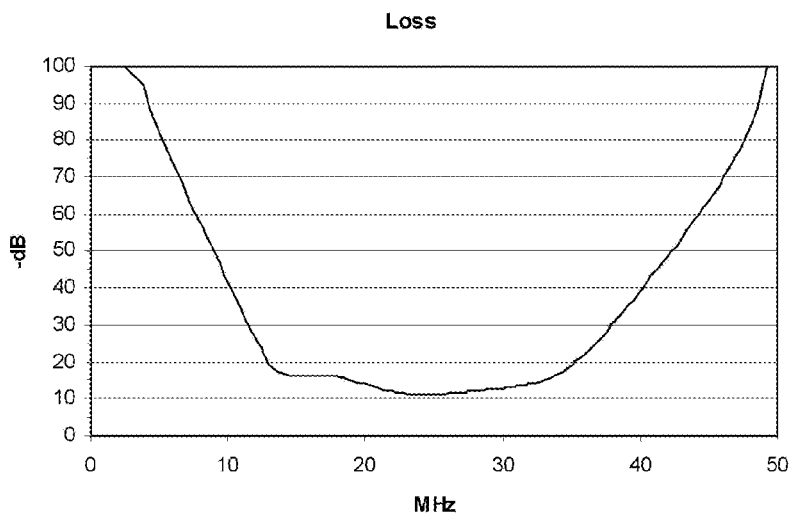
Figure 13A:
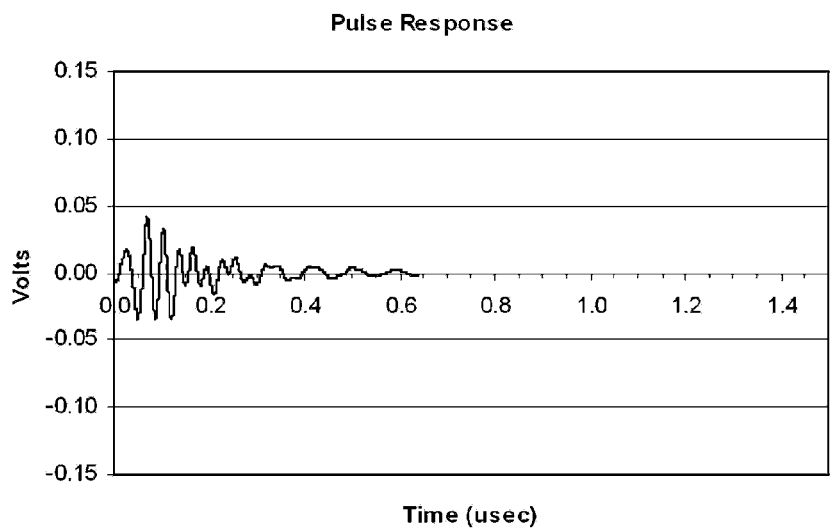
FIGS. 13A-13C are exemplary plots of pulse response, impedance, and loss for the intravascular transducer array modeled in FIG. 12 but with imaging being performed through a 1 µm layer of gold.
Figure 13B:
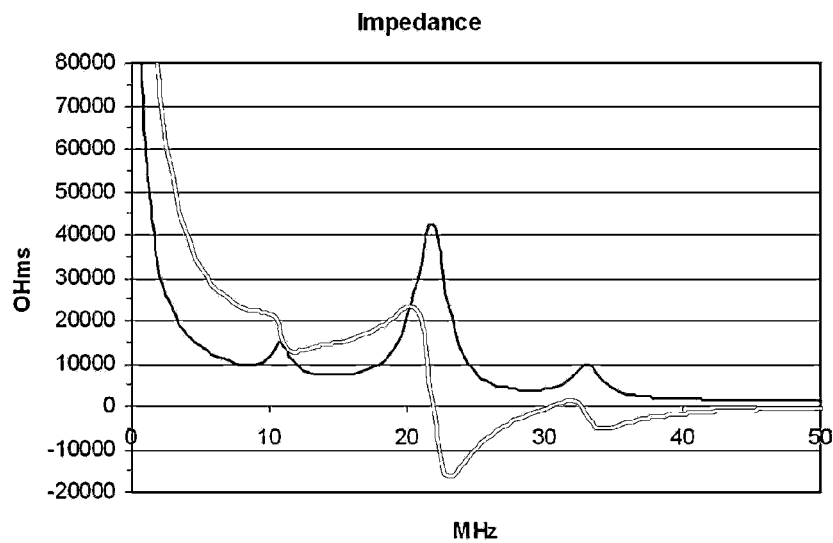
Figure 13C:
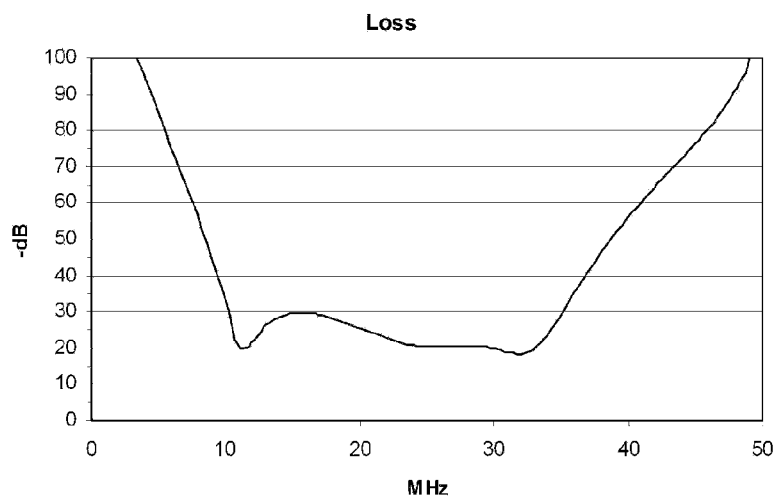
Figure 14A:
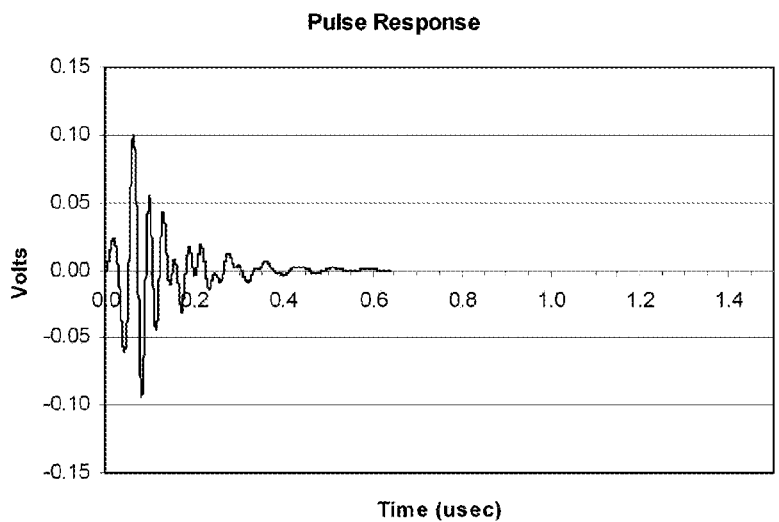
FIGS. 14A-14C are exemplary plots of pulse response, impedance, and loss for the intravascular transducer array modeled in FIG. 12 but with imaging being performed through a 1.5 µm layer of titanium.
Figure 14B:
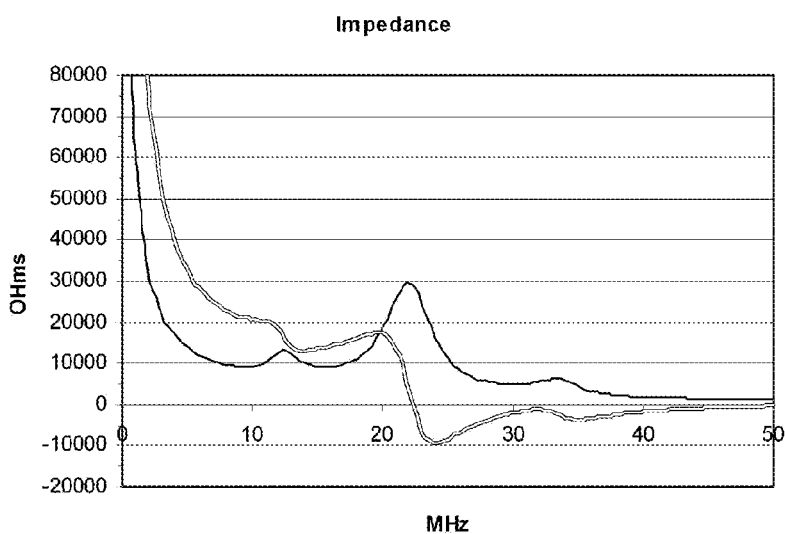
Figure 14C:
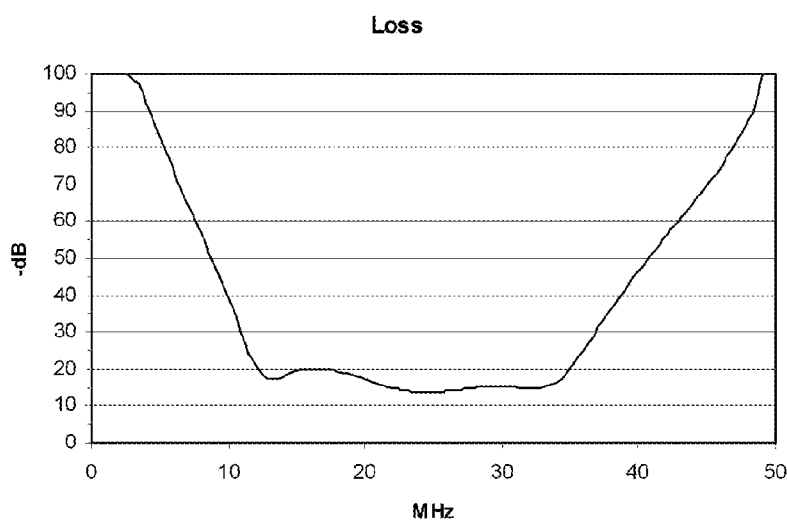
Figure 15:
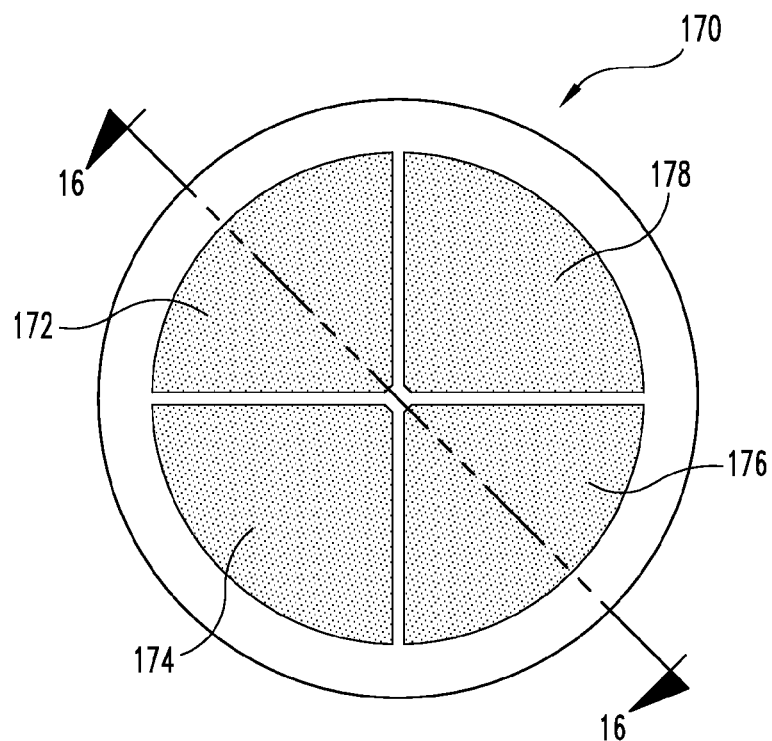
FIG. 15 is an end view of a smoothly curved tip without a guidewire lumen looking proximally along the longitudinal axis.

The pulse response, impedance, and loss were modeled on a computer for a 2D ultrasound transducer array using piezoelectric ceramic with high dielectric constant ($3500\varepsilon_0$) and with the following design parameters (FIGS. 12A-12C):

Frequency: 25 MHz
Array aperture: 0.9 mm
Element Pitch: 0.050 mm
Number of elements: 324
Number of (¼)λ matching layers: 2
Element impedance electrically matched to driver.

The same array element was then modeled with the addition of an intervening layer of either gold or titanium and the results are plotted in FIGS. 13A-13C and FIGS. 14A-C, respectively. The thickness of the modeled gold layer was 1 µm and the thickness of the modeled titanium layer was 1.5 µm. The modeled results demonstrate that the 1.5 µm layer of titanium (FIGS. 14A-14C) does not significantly affect the operational properties of the array and represents an effective material choice for the device disclosed herein. The 1.0 µm layer of gold (FIGS. 13A-13C), even though thinner by 33% vs. titanium, more adversely affects the array properties. In the latter case, insertion loss is worse by 10 dB and pulse ringdown is worse by approximately 0.3 µsec. Nonetheless gold appears to be a practical option, particular if corrective techniques such as frequency filtering are implemented. Despite its worse acoustic properties, gold and the other metals mentioned in this disclosure are expected to be acceptable and can have advantages relating to the metal's material properties such as easier processing, resistance to oxidize over extended operation, and biocompatiblility.

It is to be appreciated that what has been described herein includes an endoluminal catheter for providing image guided therapy in a patient's vasculature, comprising: an elongated catheter body adapted to be inserted into a patient's vasculature, the catheter body defining a distal portion operable to be inside the patient's vasculature while a proximal portion is outside the patient; a plurality of distal facing electrodes on the distal portion for performing controlled ablation of plaque in the patient's vasculature; and a distal facing array of ultrasound imaging transducers positioned in the catheter body proximal to the electrodes and configured to transmit and receive ultrasound pulses through the electrodes to provide real time imaging information of plaque to be ablated by the electrodes. The array of transducers may have a characteristic operating frequency greater than 15 MHz, and the electrodes may each comprise a metallic layer having a thickness less than about 8 µm. The electrodes may be positioned on the distal tip of the catheter, which may have a conical or smoothly convex shape. A smoothly curved tip may function as a lens for the ultrasound, and its outer surface may define a radius of curvature of less than about 10 mm. The ultrasound array may be a planar phased array having an element density greater than 100 elements/mm$^2$. The ultrasound array may be a multi-dimensional array having at least 15 elements in at least one of the dimensions. The array may comprise a 1-D array coupled to a rotation mechanism.

What has also been described is an endoluminal catheter for providing high quality real time planar (2D) or volumetric (3D) ultrasound visualization from inside a patient, comprising: an elongated catheter body adapted to be inserted into a patient's vasculature, the catheter body defining a distal portion operable to be inside the patient while a proximal portion is outside the patient; and a multi dimensional phased array of piezoelectric elements in the distal portion of the catheter body configured to transmit and receive ultrasound pulses having a characteristic frequency greater than 20 MHz to provide real time imaging information; wherein the array defines an element density greater than 300 elements/mm$^2$. The distal portion of the catheter may define a longitudinal axis and the array may be positioned in the distal portion of the catheter such that the longitudinal axis is within the image field of the array. The piezoelectric elements may be constructed such that they are mounted to a backing layer having a number of electrically conductive pathways extending therethrough, wherein the electrically conductive pathways electrically couple each of the piezoelectric elements to corresponding pads on a circuit substrate. The circuit substrate may include at least one multiplexer/pre-amplifier IC chip electrically coupled to the circuit substrate and to cabling extending to the distal portion of the catheter, wherein the number of individual signal lines in the cabling is substantially less than the number of piezoelectric elements in the array. The number of piezoelectric elements in the array may be greater than 300 while the number of individual signal lines in the cabling is less than 100. The catheter may further include one or more distal facing electrodes.

What also has been describe is a novel method comprising: providing an array coupled to cabling via a multiplexer, the array defining a number of piezoelectric elements that is greater than the number of individual signal lines in the cabling, the piezoelectric elements operable to transmit and receive ultrasound having a characteristic frequency greater than 20 MHz and defining an element density greater than 100 elements/mm$^2$; positioning the array at a desired region within a subject's body by movement through a circulatory system, a proximal portion of the cabling being positioned outside the subject's body while the array is positioned at the desired region; ultrasonically interrogating an internal portion of the subject's body with the array; transmitting a plurality of signals between the array and equipment coupled to the proximal portion of the cabling outside the subject's body; and displaying one or more images corresponding to the internal portion as a function of the signals. The internal portion of the subject's body comprises a blood vessel or the heart. A procedure may be performed on the internal portion while displaying the one or more images. For example, the array may be positioned in a catheter and the procedure may involve activating one or more ablation electrodes positioned on an outer surface of the catheter. A plurality of selectively operable electrodes may be provided and the procedure may include selecting which ones of the electrodes to activate based on the displayed images. The interrogation may occur through a thin layer of metallic material on an outer surface of the catheter comprising a portion of an electrode or more preferably a plurality of spaced apart electrodes.

What has also been described is a novel device for performing guided tissue ablation, comprising: an elongated body having a distal portion adapted to be inserted into a lumen of a human subject while a proximal portion is outside the subject, the elongated body having a distal portion having an outer diameter less than 5 mm and configured to be positioned inside the subject's blood vessel while a proximal portion is outside the patient, the distal portion defining a distal tip; at least one therapy electrode on the distal tip operable to deliver therapeutic energy to tissue adjacent the distal tip; and a two dimensional array of piezoelectric elements in the body proximal to the therapy electrodes and operable to transmit and receive ultrasound having a frequency greater than 20 MHz to provide real time imaging information of tissue in front of the vascular structure near the RF electrodes; wherein the therapy electrode comprises a thin layer of metallic material positioned such that at least a portion of the ultrasound received by the transducers and used for imaging passes through the thin layer of metallic material. The distal tip may comprise synthetic material and a thin layer of ceramic material may be provided to thermally insulate the synthetic material from heat generated by the electrode.

Another novel method described herein includes providing an elongated body comprising an electrode in front of an ultrasound imaging array; positioning the RF electrode at a desired region within a subject's body by movement through a circulatory system; transmitting and receiving ultrasound through the RF electrode with the array to interrogate an internal portion of the subject's body; and displaying one or more images corresponding to the internal portion. The ultrasound frequency may be at least 20 MHz, and the array may be a forward facing 2-D array. The array may be operated as a fully sampled array or a sparse array. Synthetic aperture imaging and phasing in more than one direction may be employed. A plurality of electrodes may be provided, and the operator may selectively operate one of the electrodes based on the images. The electrodes may be used to ablate arterial plaque.

What has also been described is a medical device adapted to cross a vascular occlusion comprising: an intravascular catheter having a proximal end, a distal end, and a distal tip; one or more ablation electrodes on the distal tip of the catheter, wherein the electrodes are configured to deliver energy sufficient to ablate portions of the occlusion and thereby assist the catheter in crossing the occlusion; and an ultrasound array located at the distal end of the catheter proximal to the electrodes, wherein the array is configured to provide real-time imaging of the occlusion by transmitting and receiving ultrasound through the electrodes, wherein the ultrasound has a frequency greater than 15 MHz. The medical device of claim 44 wherein the proximal end is coupled to an ultrasound imaging system and the array is phased in at least one dimension. The array may be configured to provide real time planar (2D) or volumetric (3D) imaging of an area distal to the distal tip.

What is claimed is:

1. An endoluminal catheter for providing image-guided therapy in a patient's vasculature comprising:
    an elongated catheter body adapted to be inserted into a patient's vasculature, the catheter body defining a distal portion operable to be inside the patient's vasculature while a proximal portion is outside the patient;
    a round, conical, distal facing face, on the distal tip, defining a radial center, and bearing separately-controllable electrodes for performing controlled ablation of plaque in the patient's vasculature, each electrode extending along the distal facing face, away from the radial center in a direction different from the other electrodes, and expanding in a circumferential dimension as the electrode extends away from the radial center;
    a distal facing array of ultrasound imaging transducers positioned in the catheter body proximal to the electrodes and configured to transmit and receive ultrasound pulses through the electrodes to provide real time imaging information of plaque to be ablated by the electrodes;
    wherein the array of transducers has an optimum operating frequency between 20 and 40 MHz, and the electrodes each comprise a metallic layer having a thickness less than about 8 µm and introduce an additional loss of less than 20 dB, at both a 15 MHz operating frequency and an operating frequency between about 20 MHz and 40 MHz;
    wherein the electrodes are positioned on a convex surface that defines a radius of curvature of less than 10 mm and that functions as a lens for the ultrasound; wherein a volume between said convex surface and said array of transducers is filled with a material selected from a group comprising essentially of a high temperature plastic and a silicone rubber material; and
    whereby a catheter operator can form an image of plaque on an artery interior and in response selectively activate one or more electrodes to remove plaque along a first circumferential portion of an arterial wall, while avoiding activating an electrode along a circumferential portion of an arterial wall that does not bear plaque.

2. The catheter of claim 1, wherein the ultrasound array is a phased array having an element density greater than 100 elements/mm$^2$.

3. The catheter of claim 2, wherein the ultrasound array is planar.

4. The catheter of claim 1, wherein the ultrasound array comprises a multidimensional array having at least 15 elements in at least one of the dimensions.

5. The catheter of claim 1, wherein the ultrasound array comprises a 1-D array coupled to a rotation mechanism.

6. The catheter of claim 1 wherein the ultrasound array is conical.

7. A medical device to cross a vascular occlusion comprising:
    an intravascular catheter having a proximal end, a distal end, and a conical distal tip having a radial center;
    one or more separately activated ablation electrodes on the distal tip of the catheter, each ablation catheter extending outwardly along the distal tip, from the radial center in a direction different from that of the other electrodes, and expanding in circumferentially dimension as the electrode extends away from the radial center and wherein each of the electrodes is configured to deliver energy sufficient to ablate a portion of the occlusion, located in a direction corresponding to the direction in which the electrode extends from the radial center, and thereby assist the catheter in crossing the occlusion;
    an ultrasound array located at the distal end of the catheter proximal to the electrodes, wherein the array is configured to provide real-time imaging of the occlusion by transmitting and receiving ultrasound through the electrodes, wherein the ultrasound has a frequency greater than 15 MHz, thereby providing imagery that enables a medical device user to activate a one or more electrodes closest to the occlusion;
    wherein the array of transducers has an optimum operating frequency between 20 and 40 MHz, and the electrodes each comprise a metallic layer having a thickness less than about 8 µm and introduce an additional loss of less than 20 dB, at both a 15 MHz operating frequency and an operating frequency between about 20 MHz and 40 MHz; and
    wherein the electrodes are positioned on a convex surface that defines a radius of curvature of less than 10 mm and that functions as a lens for the ultrasound; and wherein a volume between said convex surface and said array of transducers is filled with a material selected from a group comprising essentially of a high temperature plastic and a silicone rubber material.

8. The medical device of claim 7 wherein the proximal end is coupled to an ultrasound imaging system and the array is phased in at least one dimension.

9. The catheter of claim 1, wherein the face bears four electrodes, each electrode occupying a portion of a separate quadrant of circumferential extent, of the face.

10. The catheter of claim 1, wherein said electrodes comprise a titanium layer less than 8 microns thick.

* * * * *